US006869931B1

(12) United States Patent
McCrae

(10) Patent No.: US 6,869,931 B1
(45) Date of Patent: Mar. 22, 2005

(54) INHIBITION OF ANGIOGENESIS BY HIGH MOLECULAR WEIGHT KININOGEN DOMAIN 3 PEPTIDE ANALOGS

(75) Inventor: Keith R. McCrae, Chagrin Falls, OH (US)

(73) Assignee: Temple University - Of The Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 09/461,061

(22) Filed: Dec. 15, 1999

Related U.S. Application Data

(60) Provisional application No. 60/112,427, filed on Dec. 16, 1998.

(51) Int. Cl.$^7$ .............................................. A61K 38/00
(52) U.S. Cl. .............................. 514/12; 514/12; 514/2; 530/300; 530/350; 435/7.1
(58) Field of Search ................................ 530/300, 350; 514/2, 12; 435/7.1

(56) References Cited

U.S. PATENT DOCUMENTS

| 5,596,079 A | 1/1997 | Smith et al. ................. 530/328 |
| 5,756,291 A | 5/1998 | Griffin et al. .................... 435/6 |
| 5,786,365 A | 7/1998 | Heitsch et al. ............... 514/311 |
| 5,817,748 A | 10/1998 | Miller et al. ................. 530/300 |
| 5,830,671 A | 11/1998 | Dennis et al. ................ 435/7.8 |
| 5,846,821 A | 12/1998 | Guerinot et al. .......... 435/320.1 |
| 6,143,719 A | * 11/2000 | Schmaier et al. ............ 530/300 |

FOREIGN PATENT DOCUMENTS

| JP | 7082172 | 3/1995 |
| JP | 8208692 | 8/1996 |
| WO | WO 96/41640 | 12/1996 |

OTHER PUBLICATIONS

R.W. Colman, et al., Abstract #701, "Inhibition Of Angkiogenesis By Peptides Derived From Kininogen", *Blood* vol. 92, No. 10 Supplement 1, Nov. 15, 1998.

Robert W. Colman et al., "Contact System: A Vascular Biology Modulator With Anticoagulant Profibrinolytic, Antiadhesive, and Proinflammatory Attributes", *Blood*, vol. 90, No. 10 pp. 3819–3843 (Nov. 15, 1997).

Robert W. Colman, et al., "Binding of High Molecular Weight Kininogen to Human Endothelial Cells Is Mediated via a Site within domains 2 and 3 of the Urokinase Receptor", *J. Clin. Invest.*, vol. 100, No. 6, pp. 1481–1487 (Sep. 1997).

Mohammad M.H. Khan et al., "Three noncintiguous peptides comprise binding sites on high–molecular–weight kininogen to neutrophils", *The American Physiological Society (Heart Circ. Physiol. 44)*: H145–150, vol. 275 (1998).

Yanina T. Wachtfogel et al., "High Molecular Weight Kininogen Binds to Mac–1 on Neutrophils by Its Heavy Chain (Domain 3) and Its Light Chain (Domain 5)", *The Journal of Biological Chemistry*, vol. 269, No. 30, pp. 19307–19312 (Jul. 29, 1994).

Shinji Asakura et al., "Inhibition of Cell Adhesion by High Molecular Weight Kininogen", *The Journal of Cell Biology*, vol. 116, No. 2, pp. 465–476 (Jan. 1992).

Colman et al., Contact System: A Vascular Biology Modulator With Anticoagulant, Profibrinolytic, Antiadhesive, and proinflammatory Attributes. Blood, Nov. 15, 1997. vol. 90, No. 10, pp. 3819–3843.

Lottspeich et al., "The Amino Acid Sequence of the Light Chain of Human High–Molecular–Mass Kininogen", *European Jounal of Biochemistry*, 1985, vol. 152, pp. 307–314.

Takagaki et al., "Cloning and Sequence Analysis of cDNAs for Human High Molecular Weight and Low Molecular Weight Prekininogens", *The Journal of Biological Chemistry*, Jul. 15, 1985, vol. 260, No. 14, pp. 8601–8609.

Kitamura et al., "Structural Organization of Human Kininogen Gene and a Model for its Evolution", *The Journal of Biological Chemistry*, Jul. 15, 1985, vol. 260, No. 15, pp. 8610–8617.

Auerswald et al., "Cloning, expression, and characterization of human kininogen demain 3", FEBS Letters, vol. 321, No. 1, pp. 93–97, 1993.

Satya P. Kunapuli et al., "Deletion Mutagenesis of High Molecular Weight Kininogen Light Chain", *The Journal of Biological Chemistry* vol. 268, No. 4, pp. 2486–2492 (Feb. 5, 1993).

* cited by examiner

*Primary Examiner*—Christopher S. F. Low
*Assistant Examiner*—Hope A. Robinson
(74) *Attorney, Agent, or Firm*—Drinker Biddle & Reath LLP

(57) ABSTRACT

Peptide analogs the high molecular weight kininogen domain 3 are potent inhibitors of angiogenesis. The peptides have the formula (a) $X_1$-Asn-Asn-Ala-Thr-Phe-Tyr-Phe-Lys-$X_2$, (b) $X_3$-Cys-Val-Gly-Cys-$X_4$, (c) $X_5$-Leu-Asp-$X_7$-Asn-Ala-Glu-Val-Tyr-$X_6$, or (d) Tyr-Phe-Ile-Asp-Phe-Val-Ala-Arg-Glu-Thr-Thr-$X_7$-Ser-Lys-Glu-Ser wherein:

$X_1$, $X_2$, $X_3$, $X_4$, $X_5$, and $X_6$ are from zero to twelve amino acids, independently the same or different, more preferably from zero to six amino acids, and; $X_7$ is Ala or Cys.

The peptides may also comprise biologically active fragments of high molecular weight kininogen domain 3. Methods of inhibiting endothelial cell proliferation and angiogenesis are provided.

16 Claims, No Drawings

# INHIBITION OF ANGIOGENESIS BY HIGH MOLECULAR WEIGHT KININOGEN DOMAIN 3 PEPTIDE ANALOGS

CROSS-REFERENCE TO RELATED APPLICATION

The benefit of U.S. provisional patent application Ser. No. 60/112,427 filed Dec. 16, 1998 is hereby claimed. The entire disclosure of application Ser. No. 60/112,427 is incorporated herein by reference.

FIELD OF THE INVENTION

The invention relates to therapeutic compounds and methods for inhibiting angiogenesis.

BACKGROUND OF THE INVENTION

Angiogenesis

Angiogenesis is the process in which new blood vessels grow into an area which lacks a sufficient blood supply. Angiogenesis commences with the erosion of the basement membrane surrounding endothelial cells and pericytes forming capillary blood vessels. Erosion of the basement membrane is triggered by enzymes released by endothelial cells and leukocytes. The endothelial cells then migrate through the eroded basement membrane when induced by angiogenic stimulants. The migrating cells form a "sprout" off the parent blood vessel. The migrating endothelial cells proliferate, and the sprouts merge to form capillary loops, thus forming a new blood vessel.

Angiogenesis can occur under certain normal conditions in mammals such as in wound healing, in fetal and embryonic development, and in the formation of the corpus luteum, endometrium and placenta. Angiogenesis also occurs in certain disease states such as in tumor formation and expansion, or in the retina of patients with certain ocular disorders. Angiogenesis can also occur in a rheumatoid joint, hastening joint destruction by allowing an influx of leukocytes with subsequent release of inflammatory mediators.

The evidence for the role of angiogenesis in tumor growth was extensively reviewed by O'Reilly and Folkman in U.S. Pat. No. 5,639,725, the entire disclosure of which is incorporated herein by reference. It is now generally accepted that the growth of tumors is critically dependent upon this process. Primary or metastatic tumor foci are unable to achieve a size of more than approximately 2 mm in the absence of neovascularization. Serial evaluation of transgenic mice predisposed to develop neoplasms has demonstrated that neovascularization of premalignant lesions precedes their evolution into tumors (Folkman et al., *Nature* 339:58–61, 1989), and that inhibition of angiogenesis delays the growth of such lesions, as well as their assumption of a malignant phenotype (Hanahan et al., *Cell* 86:353–364, 1996). In humans, several studies have demonstrated that increased density of microvessels within a tumor is associated with a poor clinical outcome (Weidner et al., *J Natl Cancer Inst* 84:1875–1887, 1992).

An emerging paradigm is that proteolytic fragments of plasma or extracellular matrix proteins regulate angiogenesis. To date, several polypeptides with such activities have been identified. These include angiostatin, which contains kringles 1–4 plasminogen (O'Reilly et al., *Cell* 79:315–328, 1994), endostatin, a 20 kD C-terminal fragment of collagen XVIII (O'Reilly et al., *Cell* 88:277–285, 1997), PEX, the hemopexin domain of matrix metalloprotease 2 (Brooks et al., *Cell* 92:391–400, 1998), the C-terminal 16 kD fragment of prolactin (Clapp et al., *Endocrinol* 133:1292–1299, 1993) and a 29 kD fragment of fibronectin (Homandberg et al., *Am J Pathol* 120:327–332, 1985). In addition, both intact thrombospondin 1 as well as peptides derived from its procollagen domain and properdin-like type-1 repeats express potent anti-angiogenic activity (Good et al., *Proc Nat Acad Sci USA* 87:6624–6628, 1990); Tolsma et al., *J Cell Biol* 122:497–511, 1993. In preclinical models, several of these fragments inhibited tumor growth, and some induced tumor regression and dormancy (Boehm et al., *Nature* 390:404–407, 1997).

High Molecular Weight Kininogen

High molecular weight kininogen (HK) is a 120 kD glycoprotein containing heavy and light chains, comprised of domains 1 through 3, and 5and 6, respectively (Kaplan et al., *Blood* 70:1–15, 1987). The heavy and light chains are linked by domain 4, which contains bradykinin, a nonapeptide which mediates several events including NO-dependent vasodilation (Weimer et al., *J Pharm Exp Therapeutics* 262:729–733, 1992). HK (also referred to as "single chain high molecular weight kininogen") binds with high affinity to endothelial cells, where it is cleaved to two-chain high molecular weight kininogen ($HK_a$) by plasma kallikrein. Bradykinin is released from HK through cleavage mediated by plasma kallikrein (Kaplan et al., *Blood* 70:1–15, 1987). This event occurs on the surface of endothelial cells following the activation of prekallikrein to kallikrein by an endothelial cell protease (Motta et al., *Blood* 91:515–528, 1998). Cleavage of HK to form $HK_a$ and release bradykinin occurs between Lys(362) and Arg(363). $HK_a$ contains a 62 kD heavy chain and a 56 kD light chain linked by a disulfide bond.

Conversion of HK to $HK_a$ is accompanied by a dramatic structural rearrangement, which has been demonstrated using rotary shadowing electron microscopy (Weisel et al., *J. Biol Chem* 269:10100–10106, 1994). $HK_a$, but not HK, has been shown to inhibit the adhesion of endothelial and other cell types to vitronectin (Asakura, *J. Cell Biol* 116:465–476, 1992). $HK_a$, but not HK, also binds tightly to artificial anionic surfaces.

HK domain 3 consists of HK amino acids Gly(235)-Met (357). HK domain 3 has the following amino acid sequence:

Gly-Lys-Asp-Phe-Val-Gln-Pro-Pro-Thr-Lys-Ile-Cys-Val-Gly-Cys-Pro-Arg-Asp-Ile-Pro-Thr-Asn-Ser-Pro-Glu-Leu-Glu-Glu-Thr-Leu-Thr-His-Thr-Ile-Thr-Lys-Leu-Asn-Ala-Glu-Asn-Asn-Ala-Thr-Phe-Tyr-Phe-Lys-Ile-Asp-Asn-Val-Lys-Lys-Ala-Arg-Val-Gln-Val-Val-Ala-Gly-Lys-Lys-Tyr-Phe-Ile-Asp-Phe-Val-Ala-Arg-Glu-Thr-Thr-Cys-Ser-Lys-Glu-Ser-Asn-Glu-Glu-Leu-Thr-Glu-Ser-Cys-Glu-Thr-Lys-Lys-Leu-Gly-Gln-Ser-Leu-Asp-Cys-Asn-Ala-Glu-Val-Tyr-Val-Val-Pro-Trp-Glu-Lys-Lys-Ile-Tyr-Pro-Thr-Val-Asn-Cys-Gln-Pro-Leu-Gly-Met (SEQ ID NO:18).

HK binds to endothelial cells, platelets and neutrophils in the intravascular compartment. A specific cell attachment site has been identified on HK domain 3 by an antibody-directed strategy utilizing an antibody HKH15, selected for its ability to block HK binding to cells (Herwald et al., *J. Biol Chem* 270:14634–14642 (1995). A series of HK domain 3 synthetic peptides was examined for ability to inhibit biotin-HK from binding to human umbilical vein endothelial cells. As a result, the cell binding site was localized to a domain 3 segment containing HK amino acids Leu(331)-Met(357). Other weakly inhibiting peptides include Lys(224)-Pro(254), Asn(276)-Ile(301) and Leu(331)-Met(357). However, the effect on endothelial cell proliferation was not studied.

SUMMARY OF THE INVENTION

The compounds of the present invention are in the form of peptides which possess anti-angiogenic activity.

In all embodiments, the peptide may optionally comprise an amino-terminal and/or carboxy-terminal protecting group.

Compounds of the formula $X_1$-SEQ ID NO:1-$X_2$ and pharmaceutical compositions thereof are provided wherein $X_1$ is from zero to twelve amino acids, more preferably from zero to six amino acids, most preferably from zero to three amino acids;

$X_2$ is from zero to twelve amino acids, more preferably from zero to six amino acids, most preferably from zero to three amino acids; and SEQ ID NO:1 is the sequence Asn-Asn-Ala-Thr-Phe-Tyr-Phe-Lys.

In preferred compounds, $X_1$ is
(i) zero amino acids, or
(ii) the segment Thr-Leu-Thr-His-Thr-Ile-Thr-Lys-Leu-Asn-Ala-Glu (SEQ ID NO:2), or N-terminal truncation fragment thereof containing at least one amino acid, and $X_2$ is
(i) zero amino acids, or
(ii) the segment Ile-Asp-Asn-Val-Lys-Lys-Ala-Arg-Val-Gln-Val-Val (SEQ ID NO:3), or C-terminal truncation fragment thereof containing at least one amino acid.

According to a further preferred embodiment of the invention, the compound has a substantial amino acid homology to the amino acid sequence Thr-Leu-Thr-His-Thr-Ile-Thr-Lys-Leu-Asn-Ala-Glu-Asn-Asn-Ala-Thr-Phe-Tyr-Phe-Lys-Ile-Asp-Asn-Val-Lys-Lys-Ala-Arg-Val-Gln-Val-Val (SEQ ID NO:4).

According to a related invention, compounds of the formula $X_3$-SEQ ID NO:5$X_4$ and pharmaceutical compositions thereof are provided wherein $X_3$ is from zero to twelve amino acids, more preferably from zero to six amino acids, most preferably from zero to three amino acids;

$X_4$ is from zero to twelve amino acids, more preferably from zero to six amino acids, most preferably from zero to three amino acids; and SEQ ID NO:5 is the sequence Cys-Val-Gly-Cys, wherein a disulfide bond between the cysteine residues of SEQ ID NO:5 is optionally present.

In preferred compounds, $X_3$ is
(i) zero amino acids, or
(ii) the segment Gly-Lys-Asp-Phe-Val-Gln-Pro-Pro-Thr-Lys-Ile (SEQ ID NO:6), or N-terminal truncation fragment thereof containing at least one amino acid, and $X_4$ is
(i) zero amino acids, or
(ii) the segment Pro-Arg-Asp-Ile-Pro-Thr-Asn-Ser-Pro-Glu-Leu-Glu (SEQ ID NO:7), or C-terminal truncation fragment thereof containing at least one amino acid.

According to a further preferred embodiment of the invention, the compound has a substantial amino acid homology to the amino acid sequence Gly-Lys-Asp-Phe-Val-Gln-Pro-Pro-Thr-Lys-Ile-Cys-Val-Gly-Cys-Pro-Arg-Asp-Ile-Pro-Thr-Asn-Ser-Pro-Glu-Leu-Glu (SEQ ID NO:8).

According to another related invention, compounds of the formula $X_5$-Leu-Asp-$X_7$-SEQ ID NO:22-$X_6$, wherein SEQ ID NO:22 is the sequence Asn-Ala-Glu-Val-Tyr, and pharmaceutical compositions thereof are provided wherein $X_5$ is from zero to twelve amino acids, more preferably from zero to six amino acids, most preferably from zero to three amino acids;

$X_6$ is from zero to twelve amino acids, more preferably from zero to six amino acids, most preferably from zero to three amino acids; and $X_7$ is Ala or Cys.

Where $X_5$ and $X_6$ are zero amino acids, the compounds have the sequences Leu-Asp-Cys-Asn-Ala-Glu-Val-Tyr (SEQ ID NO:21) and Leu-Asp-Ala-Asn-Ala-Glu-Val-Tyr (SEQ ID NO:12).

In preferred compounds, $X_5$ is
(i) zero amino acids, or
(ii) the segment Thr-Glu-Ser-Cys-Glu-Thr-Lys-Lys-Leu-Gly-Gln-Ser (SEQ ID NO:13), or N-terminal truncation fragment thereof containing at least one amino acid, and $X_6$ is
(i) zero amino acids, or
(ii) the segment Val-Val-Pro-Trp-Glu-Lys-Lys-Ile-Tyr-Pro-Thr-Val (SEQ ID NO:14), or C-terminal truncation fragment thereof containing at least one amino acid.

According to a further preferred embodiment of the invention, the compound has a substantial amino acid homology to the amino acid sequence Thr-Glu-Ser-Cys-Glu-Thr-Lys-Lys-Leu-Gly-Gln-Ser-Leu-Asp-Ala-Asn-Ala-Glu-Val-Tyr-Val-Val-Pro-Trp-Glu-Lys-Lys-Ile-Tyr-Pro-Thr-Val (SEQ ID NO:17).

According to a related invention, the compounds Tyr-Phe-Ile-Asp-Phe-Val-Ala-Arg-Glu-Thr-Thr-Cys-Ser-Lys-Glu-Ser (SEQ ID NO:19) and Tyr-Phe-Ile-Asp-Phe-Val-Ala-Arg-Glu-Thr-Thr-Ala-Ser-Lys-Glu-Ser (SEQ ID NO:20) are provided, and pharmaceutical compositions thereof.

The invention is also directed to peptide fragments of the HK domain 3, which fragments inhibit endothelial cell proliferation and thus possess anti-angiogenic activity. In certain embodiments the peptides are from 4 to 40 amino acids in length, preferably 4 to 25 amino acids in length, more preferably from 8 to 15 amino acids in length. The fragments include certain of the compounds described above which represent segments of the HK domain 3. In an embodiment of the invention, one such peptide fragment of HK domain 3 is the compound having the amino acid sequence Tyr-Phe-Ile-Asp-Phe-Val-Ala-Arg-Glu-Thr-Thr-Cys-Ser-Lys-Glu-Ser (SEQ ID NO:19).

The invention is also directed to analogs of such fragments wherein one or more cysteine residues are replaced with alanine residues to prevent dimerization, e.g., Tyr-Phe-Ile-Asp-Phe-Val-Ala-Arg-Glu-Thr-Thr-Ala-Ser-Lys-Glu-Ser (SEQ ID NO:20).

Preferred compounds include:
(i) Asn-Asn-Ala-Thr-Phe-Tyr-Phe-Lys (SEQ ID NO:1);
(ii) Thr-Ile-Thr-Lys-Leu-Asn-Ala-Glu-Asn-Asn-Ala-Thr-Phe-Tyr-Phe-Lys (SEQ ID NO:9);
(iii) Asn-Asn-Ala-Thr-Phe-Tyr-Phe-Lys-Ile-Asp-Asn-Val-Lys-Lys-Ala-Arg (SEQ ID NO:10);
(iv) Cys-Val-Gly-Cys (SEQ ID NO:5), wherein a disulfide bond is optionally present between the cysteine residues of SEQ ID NO:5;
(v) Thr-Lys-Ile-Cys-Val-Gly-Cys-Pro-Arg-Asp-Ile-Pro-Thr-Asn-Ser-Pro (SEQ ID NO:11, wherein a disulfide bond is optionally present between the cysteine residues of said sequence);

(vi) Leu-Asp-Ala-Asn-Ala-Glu-Val-Tyr (SEQ ID NO:12);
(vii) Glu-Thr-Lys-Leu-Gly-Gln-Ser-Leu-Asp-Ala-Asn-Ala-Glu-Val-Tyr (SEQ ID NO:15);
(viii) Leu-Asp-Ala-Asn-Ala-Glu-Val-Tyr-Val-Val-Pro-Trp-Glu-Lys-Lys-Ile (SEQ ID NO:16);
(ix) Tyr-Phe-Ile-Asp-Phe-Val-Ala-Arg-Glu-Thr-Thr-Cys-Ser-Lys-Glu-Ser (SEQ ID NO:19); and
(x) Tyr-Phe-Ile-Asp-Phe-Val-Ala-Arg-Glu-Thr-Thr-Ala-Ser-Lys-Glu-Ser (SEQ ID NO:20).

The disulfide bond between the cysteine residues of the compounds containing the Cys-Val-Gly-Cys segment is preferably present. Thus, the peptide of SEQ ID NO:5 preferably has the cyclic structure:

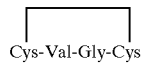

and the compounds containing the cyclized SEQ ID NO:5 segment preferably have the structure:

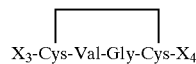

The invention also encompasses a method of inhibiting endothelial cell proliferation comprising contacting endothelial cells with the D3-peptides of the present invention.

The invention also encompasses a method of inducing apoptosis of endothelial cells comprising contacting endothelial cells with a D3-peptide.

The invention is also a composition comprising a pharmaceutically effective carrier and a D3-peptide.

In the D3-peptides, $X_1$, $X_2$, $X_3$, $X_4$, $X_5$, and $X_6$ are chains of amino acids containing from zero to twelve amino acids. The amino acids in each chain may be independently the same or may be different. In other words, each amino acid in the $X_n$ chain may be any amino acid, unless specified otherwise.

The invention is also a method of inhibiting angiogenesis in a mammal in need of such treatment comprising administering to said mammal a therapeutically effective amount of a composition comprising a pharmaceutically effective carrier and a D3-peptide. The mammal treated is preferably a human being.

Other aspects and advantages of the present invention are described in the drawings and in the following detailed description of the preferred embodiments thereof.

Abbreviations and Short Forms

The following abbreviations and short forms are used in this specification.

"bFGF" is recombinant human basic fibroblast growth factor.

"HK" means the mature form of high molecular weight kininogen, and any allelic variations thereof. By "mature" is meant the post-translationally-modified form of HK which results from cleavage of an eighteen amino acid leader from the initially translated molecule. All numbering with respect to amino acid positions of HK is from the N-terminus of the mature form as position 1. "HK" is synonymous with "single chain HK", the mature form of high molecular weight kininogen prior to cleavage by kallikrein and the formation of two-chain high molecular weight kininogen.

"$HK_a$" means two-chain high molecular weight kininogen, the product of kallikrein cleavage of mature high molecular weight kininogen, and any allelic variations thereof.

"HUVEC" means human umbilical vein endothelial cell.

Amino Acid Abbreviations

The nomenclature used to describe polypeptide compounds of the present invention follows the conventional practice wherein the amino group is presented to the left and the carboxy group to the right of each amino acid residue. In the formulae representing selected specific embodiments of the present invention, the amino-and carboxy-terminal groups, although not specifically shown, will be understood to be in the form they would assume at physiologic pH values, unless otherwise specified. In the amino acid structure formulae, each residue is generally represented by a one-letter or three-letter designation, corresponding to the trivial name of the amino acid, in accordance with the following schedule:

| A | Alanine | Ala |
|---|---|---|
| C | Cysteine | Cys |
| D | Aspartic Acid | Asp |
| E | Glutamic Acid | Glu |
| F | Phenylalanine | Phe |
| G | Glycine | Gly |
| H | Histidine | His |
| I | Isoleucine | Ile |
| K | Lysine | Lys |
| L | Leucine | Leu |
| M | Methionine | Met |
| N | Asparagine | Asn |
| P | Proline | Pro |
| Q | Glutamine | Gln |
| R | Arginine | Arg |
| S | Serine | Ser |
| T | Threonine | Thr |
| V | Valine | Val |
| W | Tryptophan | Trp |
| Y | Tyrosine | Tyr |

Definitions

The following definitions, of terms used throughout the specification, are intended as an aid to understanding the scope and practice of the present invention.

"Angiogenesis" means the generation of new blood vessels into a tissue or organ.

"Apoptosis" means a process of programmed cell death.

"D3 peptide" means a peptide of the formula (a) $X_1$-SEQ ID NO:1-$X_2$, (b) $X_3$-SEQ ID NO:5-$X_4$, (C) $X_5$-Leu-Asp-$X_7$-SEQ ID NO:22-$X_6$ were $X_1$, $X_2$, $X_3$, $X_4$, $X_5$, $X_6$ and $X_7$ are defined above, or (d) peptide fragment (or analog thereof) of HK domain 3 which is active in inhibiting endothelial cell proliferation and/or inhibiting angiogenesis.

A "peptide" is a compound comprised of amino acid residues covalenfly linked by peptide bonds.

The expression "amino acid" as used herein is meant to include both natural and synthetic amino acids, and both D and L amino acids. "Natural amino acid" means any of the twenty primary, naturally occurring amino acids which typically form peptides, polypeptides, and proteins. "Synthetic amino acid" means any other amino acid, regardless of whether it is prepared synthetically or derived from a natural source. As used herein, "synthetic amino acid" also encompasses chemically modified amino acids, including but not limited to salts, derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half life without adversely affecting their activity. Additionally, a disulfide linkage may be present or absent in the peptides of the invention, as long as anti-angiogenic activity is maintained.

Amino acids have the following general structure:

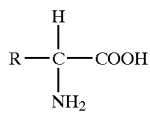

Amino acids are classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group. Peptides comprising a large number of amino acids are sometimes called "polypeptides". The amino acids of the peptides described herein and in the appended claims are understood to be either D or L amino acids with L amino acids being preferred.

"Homology" means similarity of sequence reflecting a common evolutionary origin. Peptides or proteins are said to have homology, or similarity, if a substantial number of their amino acids are either (1) identical, or (2) have a chemically similar R side chain. Nucleic acids are said to have homology if a substantial number of their nucleotides are identical.

As used herein, "protected" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., *The Peptides*, vol. 3, pp. 3–88 (Academic Press, New York, 1981) for suitable protecting groups.

As used herein, "protected" with respect to a terminal carboxyl group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

"Substantial amino acid sequence homology" means an amino acid sequence homology greater than about 30%, preferably greater than about 60%, more preferably greater than about 80%, and most preferably greater than about 90%.

By "N-terminal truncation fragment" with respect to an amino acid sequence is meant a fragment obtained from a parent sequence by removing one or more amino acids from the N-terminus thereof.

By "C-terminal truncation fragment" with respect to an amino acid sequence is meant a fragment obtained from a parent sequence by removing one or more amino acids from the C-terminus thereof.

DETAILED DESCRIPTION OF THE INVENTION

According to the present invention, peptide analogs of certain sites in the HK domain 3 inhibit endothelial cell proliferation and may also induce endothelial cell apoptosis. These activities confer upon the D3 peptides the ability to inhibit cytokine-driven angiogenesis in vivo.

Antiproliferative effects are observed at concentrations at least as low as 50 $\mu$M.

The mature human HK amino acid sequence is set forth in the recent review by Colman and Schmaier, *Blood*, 90:3819–3843 (1997), for example, the entire disclosure of which is incorporated herein by reference. $HK_a$ generated by plasma kallikrein cleavage of HK differs from HK in that it lacks the nine amino acid segment comprising HK amino acids 363–371. This segment is released from HK as the nonapeptide bradykinin. The two chains of HK resulting from the elimination of bradykinin remain linked by a disulfide bond between cysteine residues at positions 10 and 656 of mature HK. The N-terminal and C-terminal chains of $HK_a$ generated by plasma kallikrein cleavage of HK and release of bradykinin are known as HK "heavy" and "light" chains, respectively.

HK domain 3 spans HK residues 235–357. Located within domain 5 are three segments characterized by the sequences Asn-Asn-Ala-Thr-Phe-Tyr-Phe-Lys (SEQ ID NO:1), Cys-Val-Gly-Cys (SEQ ID NO:5), and Leu-Asp-Cys-Asn-Ala-Glu-Val-Tyr (SEQ ID NO:21) comprising domain 3 amino acids Asn(275)-Lys(282), Cys(246)-Cys(249) and Leu(331)-Tyr(338), respectively. Peptides containing these sequences, or analogs wherein one or more cysteine residues are replaced with alanine residues, inhibit endothelial cell proliferation and are useful as anti-angiogenic agents. The segment Tyr(299)-Ser(314) also inhibits endothelial cell proliferation, as demonstrated by the activity of SEQ ID NO:20, which corresponds to the segment Tyr(299)-Ser(314) but for the substitution of an alanine residue for Cys(310) in the native sequence.

It is believed that the peptides also induce endothelial cell apoptosis. This contributes to their utility as anti-angiogenic agents.

The D3 peptides may be recombinant peptides, natural peptides, or synthetic peptides. They may also be chemically synthesized, using, for example, solid phase synthesis methods.

In conventional solution phase peptide synthesis, the peptide chain can be prepared by a series of coupling reactions in which the constituent amino acids are added to the growing peptide chain in the desired sequence. The use of various N-protecting groups, e.g., the carbobenzyloxy group or the t-butyloxycarbonyl group, various coupling reagents (e.g., dicyclohexylcarbodiimide or carbonyldimidazole, various active esters, e.g., esters of N-hydroxyphthalimide or N-hydroxy-succinimide, and the various cleavage reagents, e.g., trifluoroacetic acid (TFA), HCl in dioxane, boron tris-(trifluoracetate) and cyanogen bromide, and reaction in solution with isolation and purification of intermediates is well-known classical peptide methodology. The preferred peptide synthesis method follows conventional Merrifield solid-phase procedures. See Merrifield, *J. Amer. Chem. Soc.* 85:2149–54 (1963) and *Science* 50:178–85 (1965). Additional information about the solid phase synthesis procedure can be had by reference to the treatise by Steward and Young (*Solid Phase Peptide Synthesis*, W.H. Freeman & Co., San Francisco, 1969, and the review chapter by Merrifield in *Advances in Enzymology* 32:221–296, F. F. Nold, Ed., Interscience Publishers, New York, 1969; and Erickson and Merrifield, *The Proteins* 2:255 et seq. (ed. Neurath and Hill), Academic Press, New York, 1976. The synthesis of peptides by solution methods is described in Neurath et al., eds. (*The Proteins*, Vol. II, 3d Ed., Academic Press, NY (1976)).

Crude peptides may be purified using preparative high performance liquid chromatography. The amino terminus may be blocked according, for example, to the methods described by Yang et al. (*FEBS Lett.* 272:61–64 (1990)).

Peptide synthesis includes both manual and automated techniques employing commercially available peptide synthesizers. The D3 peptides of the invention may be prepared by chemical synthesis and biological activity can be tested using the methods disclosed herein.

Alternatively, the D3 peptides may be prepared utilizing recombinant DNA technology, which comprises combining a nucleic acid encoding the peptide thereof in a suitable vector, inserting the resulting vector into a suitable host cell, recovering the peptide produced by the resulting host cell, and purifying the polypeptide recovered. The techniques of recombinant DNA technology are known to those of ordinary skill in the art. General methods for the cloning and expression of recombinant molecules are described in Maniatis (*Molecular Cloning*, Cold Spring Harbor Laboratories, 1982), and in Sambrook (*Molecular Cloning*, Cold Spring Harbor Laboratories, Second Ed., 1989), and in Ausubel (*Current Protocols in Molecular Biology*, Wiley and Sons, 1987), which are incorporated by reference. The complete cDNA of human HK is reported, for example, by Takagi et al., *J. Biol. Chem.* 260:8601–8609 (1985), the entire disclosure of which is incorporated herein by reference. From this nucleic acid sequence, synthetic genes encoding D3-derived peptides may be synthesized directly on a DNA synthesizer, or may be synthesized as complementary oligonucleotides which are ligated together to form the synthetic gene.

The nucleic acids encoding D3-derived peptides may be operatively linked to one or more regulatory regions. Regulatory regions include promoters, polyadenylation signals, translation initiation signals (Kozak regions), termination codons, peptide cleavage sites, and enhancers. The regulatory sequences used must be functional within the cells of the vertebrate to be immunized. Selection of the appropriate regulatory region or regions is a routine matter, within the level of ordinary skill in the art.

Promoters that may be used in the present invention include both constitutive promoters and regulated (inducible) promoters. The promoters may be prokaryotic or eukaryotic depending on the host. Among the prokaryotic (including bacteriophage) promoters useful for practice of this invention are lacd lacZ, T3, T7, lambda Pr' Pl' and trp promoters. Among the eukaryotic (including viral) promoters useful for practice of this invention are ubiquitous promoters (e.g. HPRT, vimentin, actin, tubulin), intermediate filament promoters (e.g. desmin, neurofilaments, keratin, GFAP), therapeutic gene promoters (e.g. MDR type, CFTR, factor VIII), tissue-specific promoters (e.g. actin promoter in smooth muscle cells), promoters which respond to a stimulus (e.g. steroid hormone receptor, retinoic acid receptor), tetracycline-regulated transcriptional modulators, cytomegalovirus immediate-early, retroviral LTR, metallothionein, SV40, E1a, and MLP promoters. Tetracycline-regulated transcriptional modulators and CMV promoters are described in WO 96/01313, U.S. Pat. Nos. 5,168,062 and 5,385,839, the entire disclosures of which are incorporated herein by reference.

Examples of polyadenylation signals that can be used in the present invention include but are not limited to SV40 polyadenylation signals and LTR polyadenylation signals.

The D3 peptides prepared by either chemical synthesis or recombinant DNA technology may then be assayed for biological activity according to the assay methods described herein.

In some embodiments, the peptides of the present invention may be used in the form of a pharmaceutically acceptable salt.

Suitable acids which are capable of forming salts with the peptides include inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid and the like.

Suitable bases capable of forming salts with the peptides include inorganic bases such as sodium hydroxide, ammonium hydroxide, potassium hydroxide and the like; and organic bases such as mono-, di- and tri-alkyl and aryl amines (e.g., triethylamine, diisopropyl amine, methyl amine, dimethyl amine and the like) and optionally substituted ethanol-amines (e.g., ethanolamine, diethanolamine and the like).

The present invention provides methods for inhibiting angiogenesis. A preferred embodiment is a method of inhibiting the proliferation of endothelial cells, or obtaining apoptosis of such cells. Accordingly, D3 peptides is administered to a patient in need of such treatment. A therapeutically effective amount of the drug may be administered as a composition in combination with a pharmaceutically carrier.

Pharmaceutically acceptable carriers include physiologically tolerable or acceptable diluents, excipients, solvents, adjuvants, or vehicles, for parenteral injection, for intranasal or sublingual delivery, for oral administration, for rectal or topical administration or the like. The compositions are preferably sterile and nonpyrogenic. Examples of suitable carriers include but are not limited to water, saline, dextrose, mannitol, lactose, or other sugars, lecithin, albumin, sodium glutamate cysteine hydrochloride, ethanol, polyols (propyleneglycol, ethylene, polyethyleneglycol, glycerol, and the like), vegetable oils (such as olive oil), injectable organic esters such as ethyl oleate, ethoxylated isostearyl alcohols, polyoxyethylene sorbitol and sorbitan esters, microcrystalline cellulose, aluminum methahydroxide, bentonite, agar-agar and tragacanth, or mixtures of these substances, and the like.

The pharmaceutical compositions may also contain minor amounts of nontoxic auxiliary substances such as welting agents, emulsifying agents, pH buffering agents, antibacterial and antifungal agents (such as parabens, chlorobutanol, phenol, sorbic acid, and the like). If desired, absorption enhancing or delaying agents (such as liposomes, aluminum monostearate, or gelatin) may be used. The compositions can be prepared in conventional forms, either as liquid solutions or suspensions, solid forms suitable for solution or suspension in liquid prior to injection, or as emulsions.

Compositions containing the anti-angiogenic D3 peptides may be administered by any convenient route which will result in delivery to the site of undesired angiogenesis in an amount effective for inhibiting that angiogenesis from proceeding. Modes of administration include, for example, orally, rectally, parenterally (intravenously, intramuscularly, intraarterially, or subcutaneously), intracisternally, intravaginally, intraperitoneally, locally (powders, ointments or drops), or as a buccal or nasal spray or aerosol. The compositions can also be delivered through a catheter for local delivery at a target site, or via a biodegradable polymer. The compositions may also be complexed to ligands, or antibodies, for targeted delivery of the compositions.

The compositions are most effectively administered parenterally, preferably intravenously or subcutaneously. For intravenous administration, they may be dissolved in any appropriate intravenous delivery vehicle containing physiologically compatible substances, such as sodium chloride, glycine, and the like, having a buffered pH compatible with physiologic conditions. Such intravenous delivery vehicles are known to those skilled in the art. In a preferred embodiment, the vehicle is a sterile saline solution. If the peptides are sufficiently small (e.g., less than about 8–10 amino acids) other preferred routes of administration are intranasal, sublingual, and the like. Intravenous or subcutaneous administration may comprise, for example, injection or infusion.

The compositions according to the invention can be administered in any circumstance in which inhibition of angiogenesis is desired. Disease states which may be treated include but are not limited to cancer, rheumatoid arthritis, and certain ocular disorders characterized by undesired vascularization of the retina. Because the peptides of the invention are anti-angiogenic, cancers characterized by the growth of solid tumors through angiogenesis of the tissue surrounding the tumor site may be treated according to the invention. The compositions according to the invention may be administered to a tumor, for example, by direct injection into the tumor, or the tissues surrounding the tumor.

The amount of active agent administered depends upon the degree of the anti-angiogenic effect desired. Those skilled in the art will derive appropriate dosages and schedules of administration to suit the specific circumstances and needs of the patient. Typically, dosages are from about 0.1 to about 100, preferably from about 0.5 to about 50, most preferably from about 1 to about 20, mg/kg of body weight. The active agent may be administered by injection daily, over a course of therapy lasting two to three weeks, for example. Alternatively, the agent may be administered by continuous infusion, such as via an implanted subcutaneous pump.

Peptides which inhibit endothelial cell proliferation with an IC50 of no more than about 100 µM, more preferably no more than about 50 µM, most preferably no more than about 10 µM, are preferred. For purposes of this preference, IC50 is determined according to the procedure and formula set forth in Examples 1–6, below.

The practice of the present invention is illustrated by the following non-limiting examples.

EXAMPLES

Materials

The materials utilized in the Examples were sourced as follows. Tissue culture medium and reagents were obtained from Mediatech (Herndon, Va.). Fetal bovine serum was from Hyclone (Logan, Utah). Recombinant human basic fibroblast growth factor (bFGF), was obtained from Collaborative Biomedical Products/Becton Dickinson (Bedford, Mass.). Gelatin was purchased from Sigma (St. Louis, Mo.).

Synthetic Peptides

Synthetic peptides were synthesized on a Rainin Symphony multiple peptide synthesizer, using Fmoc chemistry. All resins (AnaSpec) used for solid phase synthesis were Wang resins preloaded with the first amino acid. Fmoc amino acids were purchased from Perseptive Biosystems, with side chain protective groups as follows: trityl (Asn, Cys, Gln, and His), Boc (Lys and Trp), Ombu (Asp and Glu), T.U. (Ser, Thr and Tyr) and P.G. (Arg). Deprotection of the Fmoc group was performed in piperidine in dimethylformamide (DMF). Coupling was carried out done in HBTU in N-methylmorpholine/DMF as the activator. Standard synthesis cycles were 3×30" washes with DMF, 3×15" deprotection with piperidine, 6×20" DMF washes, 45 minute coupling with amino acid and activator followed by 3×30" DMF washes.

Peptides were cleaved off the solid phase support with cleavage cocktail consisting of 88:5:5:2 (TFA:water:phenol:triisopropylsilane). Cleavage was done on the synthesizer. Peptides were precipitated with ether, pelleted by centrifugation, washed three times with ether and then allowed to dry. HPLC was carried out on a Beckman HPLC system using Rainin Dynamax Reversed Phase columns and an acetonitrile gradient in water. The desired peptide was detected during elution by off line MALDI-TOF mass spectrophotometry using a Perseptive Biosystems Voyager instrument. Purified peptides were lyophilized and then reanalyzed by MALDI-TOF mass spectrophotometry.

Cell Culture Methods

Human umbilical vein endothelial cells (HUVEC) were isolated and cultured as previously described (Graham et al., Blood 91:3300–7 1998). Cells were of passage 3 or lower.

Examples 1–6

Effect of HK Domain 3 Peptide on Endothelial Cell Proliferation

A. Experimental

To assess the effect of peptides on endothelial cell proliferation, HUVEC were suspended at a concentration of 30,000 cells/ml in M199 containing 2% FCS. One hundred microliters of this suspension was then plated in individual wells of a 96 well microplate precoated with 1% gelatin. After incubation for 2 hours, at 37° C., to allow cells to adhere and spread, medium was removed and replaced with fresh M199 containing (i) 2% FCS, (ii) 10 µM $ZnCl_2$, (iii) 10 ng/ml bFGF as a growth factor, and (iv) 5, 10, 25 or 50 µM of one of the following D3 peptides:

Thr-Ile-Thr-Lys-Leu-Asn-Ala-Glu-Asn-Asn-Ala-Thr-Phe-Tyr-Phe-Lys (SEQ ID NO:9);

Asn-Asn-Ala-Thr-Phe-Tyr-Phe-Lys-Ile-Asp-Asn-Val-Lys-Lys-Ala-Arg (SEQ ID NO:10);

Thr-Lys-Ile-Cys-Val-Gly-Cys-Pro-Arg-Asp-Ile-Pro-Thr-Asn-Ser-Pro (SEQ ID NO:11);

Glu-Thr-Lys-Lys-Leu-Gly-Gln-Ser-Leu-Asp-Ala-Asn-Ala-Glu-Val-Tyr (SEQ ID NO:15);

Leu-Asp-Ala-Asn-Ala-Glu-Val-Tyr-Val-Val-Pro-Trp-Glu-Lys-Lys-Ile (SEQ ID NO:16); and Tyr-Phe-Ile-Asp-Phe-Val-Ala-Arg-Glu-Thr-Thr-Ala-Ser-Lys-Glu-Ser (SEQ ID NO:20).

Cells were then incubated for 48 hours at 37° C., at which time the relative numbers of cells in each well were determined using the Cell Titer® $Aq_{ueous}$ cell proliferation assay (Promega, Madison, Wis.). Briefly, 20 µl of a 19:1 (V/V) mixture of (3-(4,5-dimethylthiazol-2-yl)-5-(3-carboxymethylphenyl)-2-(4-sulfophenyl)-2H-tetrazolium (MTS) and phenazine methosulfate (PMS) was added to each well, and after an additional hour of incubation, $A_{490}$ was measured using a BioRad model EL311 microplate reader. The percent inhibition of cell proliferation by each peptide was determined using the formula:

$$\% \text{ inhibition} = (1 - [(A_{490\,(+GF,\,D3)} - A_{490\,(-GF)})/(A_{490\,(+GF)} - A_{490\,(-GF)})]) \times 100,$$

where (+GF) and (−GF) represent proliferation in the presence or absence of added growth factor bFGF, and (+GF, D3) represents proliferation in the presence of both growth factor and D3 peptide. The significance of differences in relative endothelial cell proliferation cell numbers at the end of the proliferation assays was determined using the Student's two-tailed T-test for paired samples. The IC50 was then calculated for each compound. Due to peptide losses during filtration, the IC50 for SEQ ID NO:9 and SEQ ID NO:10 are estimates, based upon the assumption that since these peptides contain one tyrosine residue, a 1 mM peptide concentration should have an absorbance at $A_{280}$ of 1.28 .

B. Results

The IC50 for inhibition of endothelial cell proliferation attributable to each peptide is given in Table 1. Each compound is effective at inhibiting endothelial cell proliferation.

Endothelial cell proliferation is a hallmark of angiogenesis. The inhibition of bFGF-induced endothelial cell proliferation is an accepted model of angiogenesis. Thus, the results demonstrated herein establish the anti-angiogenic activity of the D3 peptides, and their utility in medicine for inhibiting undesired angiogenesis.

TABLE 1

Inhibition of Endothelial Cell Proliferation by D3 Peptides

| Example | Inhibitor | IC50 ($\mu$M) |
|---|---|---|
| 1 | SEQ ID NO:9 | <0.8 |
| 2 | SEQ ID NO:10 | <0.8 |
| 3 | SEQ ID NO:11 | 30 |
| 4 | SEQ ID NO:15 | 42 |
| 5 | SEQ ID NO:16 | 44 |
| 6 | SEQ ID NO:20 | 28 |

All references discussed herein are incorporated by reference. One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should be made to the appended claims, rather than to the foregoing specification, as indicating the scope of the invention.

What is claimed is:

1. A pharmaceutical composition comprising a pharmaceutically acceptable carrier and a compound consisting of the formula $X_1$-SEQ ID NO:1-$X_2$ wherein
   $X_1$ is from zero to twelve amino acids, and
   $X_2$ is from zero to twelve amino acids.

2. The composition of claim 1, wherein
   $X_1$ is from zero to six amino acids, and
   $X_2$ is from zero to six amino acids.

3. The composition of claim 1 wherein
   $X_1$ is
      (i) zero amino acids, or
      (ii) the segment SEQ ID NO:2, or N-terminal truncation fragment thereof containing at least one amino acid, and
   $X_2$ is
      (i) zero amino acids, or
      (ii) the segment SEQ ID NO:3, or C-terminal truncation fragment thereof containing at least one amino acid.

4. The composition of claim 1 wherein the compound has substantial amino acid sequence homology to the amino acid sequence SEQ ID NO:4.

5. The composition of claim 1 wherein the compound has the amino acid sequence SEQ ID NO:1.

6. The composition of claim 1 wherein the compound has the amino acid sequence SEQ ID NO:9.

7. The composition of claim 1 wherein the compound has the amino acid sequence SEQ ID NO:10.

8. A method of inhibiting angiogenesis comprising administering to a mammal an effective amount of a composition according to claim 1.

9. A method of inhibiting angiogenesis comprising administering to a mammal effective amount of a composition according to claim 2.

10. A method of inhibiting angiogenesis comprising administering to a mammal effective amount of a composition according to claim 3.

11. A method of inhibiting angiogenesis comprising administering to a mammal effective amount of a composition according to claim 4.

12. A method of inhibiting angiogenesis comprising administering to a mammal effective amount of a composition according to claim 5.

13. A method of inhibiting angiogenesis comprising administering to a mammal effective amount of a composition according to claim 6.

14. A method of inhibiting angiogenesis comprising administering to a mammal effective amount of a composition according to claim 7.

15. A method for inhibiting angiogenesis comprising administering to a mammal an effective amount of a compound of the formula $X_1$-SEQ ID NO:1-$X_2$ wherein $X_1$ is from zero to twelve amino acids, and $X_2$ is from zero to twelve amino acids.

16. A method of inhibiting angiogenesis according to claim 15 wherein $X_1$ is
(i) zero amino acids, or
(ii) the segment SEQ ID NO:2, or N-terminal truncation fragment thereof containing at least one amino acid, and $X_2$ is
(i) zero amino acids, or
(ii) the segment SEQ ID NO:3, or C-terminal truncation fragment thereof containing at least one amino acid.

* * * * *

SEQUENCE LISTING

<160> NUMBER OF SEQ ID NOS: 22

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Human high
    molecular weight kininogen (HK) fragment from
    domain 3 thereof

<400> SEQUENCE: 1

Asn Asn Ala Thr Phe Tyr Phe Lys
 1               5

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Fragment of
    human HK domain 3

<400> SEQUENCE: 2

Thr Leu Thr His Thr Ile Thr Lys Leu Asn Ala Glu
 1               5                   10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Fragment of
    human HK domain 3

<400> SEQUENCE: 3

Ile Asp Asn Val Lys Lys Ala Arg Val Gln Val Val
 1               5                   10

<210> SEQ ID NO 4
<211> LENGTH: 32
<212> TYPE: PRT

-continued

```
<213> ORGANISM: Artificial Sequence
<220> FEATURE:
<223> OTHER INFORMATION: Description of Artificial Sequence: Fragment of
      human HK domain 3

<400> SEQUENCE: 4

Thr Leu Thr His Thr Ile Thr Lys Leu Asn Ala Glu Asn Asn Ala Thr
 1               5                  10                  15

Phe Tyr Phe Lys Ile Asp Asn Val Lys Lys Ala Arg Val Gln Val Val
            20                  25                  30

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Fragment of
      human HK domain 3

<400> SEQUENCE: 5

Cys Val Gly Cys
 1

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Fragment of
      human HK domain 3

<400> SEQUENCE: 6

Gly Lys Asp Phe Val Gln Pro Pro Thr Lys Ile
 1               5                  10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Fragment of
      human HK domain 3

<400> SEQUENCE: 7

Pro Arg Asp Ile Pro Thr Asn Ser Pro Glu Leu Glu
 1               5                  10

<210> SEQ ID NO 8
<211> LENGTH: 27
<212> TYPE: PRT
<213> ORGANISM: Artificial Sequence
<220> FEATURE:
<223> OTHER INFORMATION: Description of Artificial Sequence: Fragment of
      human HK domain 3

<400> SEQUENCE: 8

Gly Lys Asp Phe Val Gln Pro Pro Thr Lys Ile Cys Val Gly Cys Pro
 1               5                  10                  15

Arg Asp Ile Pro Thr Asn Ser Pro Glu Leu Glu
            20                  25

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Fragment of
```

-continued human HK domain 3

<400> SEQUENCE: 9

Thr Ile Thr Lys Leu Asn Ala Glu Asn Asn Ala Thr Phe Tyr Phe Lys
 1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Fragment of
      human HK domain 3

<400> SEQUENCE: 10

Asn Asn Ala Thr Phe Tyr Phe Lys Ile Asp Asn Val Lys Lys Ala Arg
 1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Fragment of
      human HK domain 3

<400> SEQUENCE: 11

Thr Lys Ile Cys Val Gly Cys Pro Arg Asp Ile Pro Thr Asn Ser Pro
 1               5                   10                  15

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence:  Analog of
      human HK domain 3 fragment

<400> SEQUENCE: 12

Leu Asp Ala Asn Ala Glu Val Tyr
 1               5

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Fragment of
      human HK domain 3

<400> SEQUENCE: 13

Thr Glu Ser Cys Glu Thr Lys Lys Leu Gly Gln Ser
 1               5                   10

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Fragment of
      human HK domain 3

<400> SEQUENCE: 14

Val Val Pro Trp Glu Lys Lys Ile Tyr Pro Thr Val
 1               5                   10

<210> SEQ ID NO 15

```
<211> LENGTH: 16
<212> TYPE: PRT
<213> ORGANISM: Artificial Sequence
<220> FEATURE:
<223> OTHER INFORMATION: Description of Artificial Sequence: Fragment of
      human HK domain 3

<400> SEQUENCE: 15

Glu Thr Lys Lys Leu Gly Gln Ser Leu Asp Ala Asn Ala Glu Val Tyr
 1               5                  10                  15

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Analog of
      human HK domain 3 fragment

<400> SEQUENCE: 16

Leu Asp Ala Asn Ala Glu Val Tyr Val Val Pro Trp Glu Lys Lys Ile
 1               5                  10                  15

<210> SEQ ID NO 17
<211> LENGTH: 32
<212> TYPE: PRT
<213> ORGANISM: Artificial Sequence
<220> FEATURE:
<223> OTHER INFORMATION: Description of Artificial Sequence: Analog of
      human HK domain 3 fragment

<400> SEQUENCE: 17

Thr Glu Ser Cys Glu Thr Lys Lys Leu Gly Gln Ser Leu Asp Ala Asn
 1               5                  10                  15

Ala Glu Val Tyr Val Val Pro Trp Glu Lys Lys Ile Tyr Pro Thr Val
                20                  25                  30

<210> SEQ ID NO 18
<211> LENGTH: 123
<212> TYPE: PRT
<213> ORGANISM: Artificial Sequence
<220> FEATURE:
<223> OTHER INFORMATION: Description of Artificial Sequence: Human HK
      domain 3

<400> SEQUENCE: 18

Gly Lys Asp Phe Val Gln Pro Pro Thr Lys Ile Cys Val Gly Cys Pro
 1               5                  10                  15

Arg Asp Ile Pro Thr Asn Ser Pro Glu Leu Glu Glu Thr Leu Thr His
                20                  25                  30

Thr Ile Thr Lys Leu Asn Ala Glu Asn Ala Thr Phe Tyr Phe Lys
            35                  40                  45

Ile Asp Asn Val Lys Lys Ala Arg Val Gln Val Val Ala Gly Lys Lys
 50                  55                  60

Tyr Phe Ile Asp Phe Val Ala Arg Glu Thr Thr Cys Ser Lys Glu Ser
 65                  70                  75                  80

Asn Glu Glu Leu Thr Glu Ser Cys Glu Thr Lys Lys Leu Gly Gln Ser
                85                  90                  95

Leu Asp Cys Asn Ala Glu Val Tyr Val Val Pro Trp Glu Lys Lys Ile
                100                 105                 110

Tyr Pro Thr Val Asn Cys Gln Pro Leu Gly Met
            115                 120
```

```
-continued

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Human HK
      domain 3

<400> SEQUENCE: 19

Tyr Phe Ile Asp Phe Val Ala Arg Glu Thr Thr Cys Ser Lys Glu Ser
 1               5                  10                  15

<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: Analog of
      human HK domain 3 fragment

<400> SEQUENCE: 20

Tyr Phe Ile Asp Phe Val Ala Arg Glu Thr Thr Ala Ser Lys Glu Ser
 1               5                  10                  15

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Fragment of
      human HK domain 3

<400> SEQUENCE: 21

Leu Asp Cys Asn Ala Glu Val Tyr
 1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Fragment of
      human HK domain 3

<400> SEQUENCE: 22

Asn Ala Glu Val Tyr
 1               5
```